United States Patent
Castillo Zambudio et al.

(10) Patent No.: US 11,041,805 B2
(45) Date of Patent: Jun. 22, 2021

(54) METHOD AND SYSTEM FOR DETERMINING PH VALUES OF FERMENTED/ACIDIFIED ANIMAL/VEGETABLE MILK PRODUCTS FROM INLINE OPTICAL MEASUREMENTS

(71) Applicant: UNIVERSITAT AUTONOMA DE BARCELONA, Bellaterra (ES)

(72) Inventors: Manuel Castillo Zambudio, Bellaterra (ES); Oscar Arango Bedoya, Cerdanyola del Vallès (ES); Antonio José Trujillo Mesa, Sant Feliu de Llobregat (ES)

(73) Assignee: UNIVERSITAT AUTONOMA DE BARCELONA, Bellaterra (ES)

(*) Notice: Subject to any disclaimer, the term of this patent is extended or adjusted under 35 U.S.C. 154(b) by 269 days.

(21) Appl. No.: 15/778,402

(22) PCT Filed: Nov. 24, 2016

(86) PCT No.: PCT/EP2016/078712
§ 371 (c)(1),
(2) Date: May 23, 2018

(87) PCT Pub. No.: WO2017/089483
PCT Pub. Date: Jun. 1, 2017

(65) Prior Publication Data
US 2018/0340887 A1    Nov. 29, 2018

(30) Foreign Application Priority Data
Nov. 26, 2015  (EP) .................................. 15196442

(51) Int. Cl.
*G01N 21/51*    (2006.01)
*G01N 33/04*    (2006.01)
(Continued)

(52) U.S. Cl.
CPC .............. *G01N 21/51* (2013.01); *G01N 21/80* (2013.01); *G01N 33/04* (2013.01); *A23C 9/1307* (2013.01); *G01N 21/82* (2013.01)

(58) Field of Classification Search
CPC ........ G01N 21/51; G01N 33/04; G01N 21/80; G01N 21/82; A23C 9/1307
See application file for complete search history.

(56) References Cited

U.S. PATENT DOCUMENTS

2008/0268110 A1    10/2008  Castillo et al.
2009/0255473 A1*   10/2009  Katz ................... G01N 21/359
                                                                  119/14.08
2015/0088472 A1     3/2015  Payne

FOREIGN PATENT DOCUMENTS

EP         0947822 A1      10/1999
WO    WO-2015000695 A1      1/2015

OTHER PUBLICATIONS

Shah et al (Introduction to Fiber Optics: Sensors for biomedical applications, Indian Journal of Pharmaceutical Sciences, 2011, 73(1), pp. 17-22) (Year: 2011).*

(Continued)

*Primary Examiner* — Benjamin R Whatley
*Assistant Examiner* — Jean Caraballo-Leon
(74) *Attorney, Agent, or Firm* — Harness, Dickey & Pierce, P.L.C.

(57) ABSTRACT

A method (100) and a system for determining pH values of fermented/acidified animal/vegetable milk products from inline optical measurements, the method comprising: emitting light into a fermented/acidified animal/vegetable milk product (101); optically detecting scattering light coming from said fermented/acidified animal/vegetable milk product, generated from said emitted light once received therein, to collect scattered light data (102); calculating by a computing device including one or more processors running an (Continued)

algorithm at least one value of a variable from the collected scattered light data (103); and obtaining, by said computing device a pH value of the fermented/acidified animal/vegetable milk product by using said at least one calculated value of a variable (104), wherein a single wavelength is used for collecting the scattered light data.

19 Claims, 3 Drawing Sheets

(51) Int. Cl.
   *G01N 21/80* (2006.01)
   *A23C 9/13* (2006.01)
   *G01N 21/82* (2006.01)

(56) References Cited

OTHER PUBLICATIONS

Moitzi et al (The pH Induced Sol-Gel Transition in Skim Milk Revisited. A Detailed Study Using Time-Resolved Light and X-ray Scattering Experiments, Langmuir, 2011, 27, 6 pp. 2195-2203) (Year: 2011).*
International Search Report and Written Opinion of the International Searching Authority issued in PCT/EP2016/078712, dated Feb. 10, 2017; ISA/EPO.
Anon. (2003). Dairy Processing Handbook, 2nd revised edn, Tetra Pak Processing Systems AB, Lund, Sweden.
Castillo, M.; Payne, F. A.; Hicks, C. L.; Laencina, J.; Lopez, M. B. (2002). Effect of calcium and enzyme in cutting time prediction of coagulating goats' milk using a light scattering sensor. International Dairy Journal, 12: 1019-1023.
Castillo, M.; Payne, F. A.; Hicks, C. L.; Lopez, M. B. (2000). Predicting cutting and clotting time of coagulating goats' milk using diffuse reflectance: Effect of pH, temperature and enzyme concentration. International Dairy Journal, 10: 551-562.
Cimander, C.; Carlsson, M.; Mandenius, C. (2002). Sensor fusion for online monitoring of yoghurt fermentation. Journal of Biotechnology 99: 237-248.
De Brabandere, A.G.; de Baerdemaeker, J.G. (1999). Effects of process conditions on the pH development during yogurt fermentation. J. Food Eng. 41: 221-227.
Horne, D. S. (1998). Casein interactions: Casting light on the Black Boxes, the structure in dairy products. Int. Dairy J. 8:171-177.
Lee, W. J.; Lucey, J. A. (2010). Formation and physycal properties of yogurt. Asian—Aust. J. Anim. Sci., 23(9): 1127-1136.
Lucey, J. A. (2004). Formation, structural properties and rheology of acid-coagulated milk gels. In Cheese: Chemistry, Physics and Microbiology. vol. 1. General Aspects (Ed. P. F. Fox, P. L. H. McSweeney, T. M. Cogan and T. P. Guinee). 3rd ed. Elsevier Academic Press, London. pp. 105-122.
Lucey, J.; Tamehana, M.; Singh, H.; Munro, P. (1998). Effect of interactions between denatured whey proteins and casein micelles on the formation and rheological properties of acid skim milk gels. J. Dairy Res. 65:555-567.
Mulvihill, D. M. and M. B. Grufferty. (1995). Effect of thermal processing on the coagulability of milk by acid. In Heatinduced Changes in Milk. Special Issue No. 9501 (Ed. P. F. Fox). International Dairy Federation, Brussels. pp. 188-205.
Navrátil, M.; Cimander, C.; Mandenius, C. (2004). Online Multisensor Monitoring of Yogurt and Filmjölk Fermentations on Production Scale. J. Agric. Food Chem. 52: 415-420.
Nicolau, N.; Castillo, M.; Buffa, M; O'Callaghan, D. J.; Guamis, B. (2010). Estudio de la coagulación de leche de oveja mediante monitorización con un sensor óptico. Actas del VI Congreso Español de Ingeniería de Alimentos, Logroño, España. ISBN: 978-84-7359-654-1.
O'Callaghan, D. J.; O'Donnell, C. P.; Payne, F. A. (2000). Online sensing techniques for coagulum setting in renneted milks. Journal of Food Engineering, 43: 155-165.
O'Callaghan, D. J.; O'Donnell, C. P.; Payne, F. A. (1999). A comparison of online techniques for determination of curd setting time using cheese milks under different rates of coagulation. Journal of Food Engineering, 41: 43-54.
Payne, F. A.; Castillo M. 2007. Light backscatter sensor applications in milk coagulation. In: Encyclopedia of Agricultural, Food, and Biological Engineering. vol. 1, Edition 1, pp. 1-5. Heldman, D., Ed. Taylor & Francis Group, Boca Raton. ISBN: 978-0-8247-0938-9 (hardback); 978-0-8247-0937-2 (electronic).
Payne, F.A.; Hicks, C.L.; Shen, P.S. (1993). Predicting optimal cutting time of coagulating milk using diffuse reflectance. J. Dairy Sci. 7648-7661.
Payne, F.A.; Madangopal, S.; Hicks, C.L.; Shearer, S.A. (1990). Fiber optic milk coagulation sensor for cut-time detection. Food Processing Automation Conference, American Society of Agricultural Engineers, St. Joseph. Michigan, Publication 02-90, 173.
Shao, Y.; He, Y. (2009). Measurement of Soluble Solids Content and pH of Yogurt Using Visible/Near Infrared Spectroscopy and Chemometrics. Food Bioprocess Technol 2: 229-233.
Soukoulis, C.; Panagiotidis, P.; Koureli, R.; Tzia, C. (2007). Industrial yogurt manufacture: Monitoring of fermentation process and improvement of final product quality. J. Dairy Sci. 90, 2641-2654.
Tabayehnejad, N.; Castillo, M.; Payne, F. A. (2011). Comparison of total milk-clotting activity measurement precision using the Berridge clotting time method and a proposed optical method. Journal of Food Engineering, 108: 549-556.
Walstra, P.; Wouters, J.T.M.; Geurts, T.J. (2006a). Chapter 22 Fermented milks. In Dairy Science and Technology; Taylor & Francis Group, LLC: Boca Raton, FL, USA, pp. 551-573.
Walstra, P.; Wouters, J.T.M.; Geurts, T.J. (2006b). Chapter 11 Cooling and freezing. In Dairy Science and Technology; Taylor & Francis Group, LLC: Boca Raton, FL, USA, pp. 297-307.
Wesstrom, O. (2001). Endress+Hauser, Inc. white paper: Inline pH Measurement for the Food / Dairy and Beverage Industry.
Fox et al.; Cheese Chemistry, Physics and Microbiology, 3rd Edition; vol. 1, 2004.
Taterka Heather et al: "The effect of whey protein denaturation on light backscatter and particle size of the casein micelle as a function of pH and heat-treatment temperature", International Dairy Journal, vol. 48, Feb. 10, 2015 (Feb. 10, 2015), pp. 53-59.
Lochte-Watson K R et al: "Effects of pH, protein, fat, and calcium on diffuse reflectance of milk", Transactions of the American Society of Agricultural Engineers, American Society of Agricultural Engineers. St.Joseph, MI, us, vol. 41, No. 3, May 1998 (May 1998), pp. 701-707.
Colette C. Fagan et al: "Novel Online Sensor Technology for Continuous Monitoring of Milk Coagulation and Whey Separation in Cheesemaking", Journal of Agricultural and Food Chemistry, vol. 55, No. 22, Sep. 14, 2007 (Sep. 14, 2007), pp. 8836-8844.
O. Arango et al: "Predicting coagulation and syneresis parameters of milk gels when inulin is added as fat substitute using infrared light backscatter",Journal of Food Engineering,vol. 157, Mar. 2, 2015 (Mar. 2, 2015), pp. 63-69.
Ahmed Rabiea Abdelgawad et al: Using a fiber optic sensor for cutting time prediction in cheese manufacture from a mixture of cow, sheep and goat milk11 , Journal of Food Engineering, vol. 125, Oct. 11, 2013 (Oct. 11, 2013), pp. 157-168.

* cited by examiner

METHOD AND SYSTEM FOR DETERMINING PH VALUES OF FERMENTED/ACIDIFIED ANIMAL/VEGETABLE MILK PRODUCTS FROM INLINE OPTICAL MEASUREMENTS

CROSS REFERENCE TO RELATED APPLICATIONS

This application is a U.S. National Phase Application under 35 U.S.C. 371 of International Application No. PCT/EP2016/078712 filed on Nov. 24, 2016 and published in English as WO 2017/089483 A1 on Jun. 1, 2017. This application claims priority to European Application No. 15196442.6 filed on Nov. 26, 2015. The entire disclosures of all of the above applications are incorporated herein by reference.

TECHNICAL FIELD

The present invention is directed, in general, to the field of inline optical measurements. In particular, the invention relates to a method and system for determining pH values of fermented/acidified animal/vegetable milk products from inline optical measurements.

Gel formation process, as appearing in this description, involves the time that the fermented/acidified animal/vegetable milk product takes to gel from the addition of a starter culture in the milk product. The beginning of the gel formation process could be approximately estimated from the light backscatter profile by real time identification of the time parameter, $t_{2max}$, (first maximum of the second derivative of the light backscatter profile as a function of time).

BACKGROUND OF THE INVENTION

For the Codex *Alimentarius*, fermented/acidified animal milk is a milk product obtained by fermentation of milk, which contains starter microorganisms that shall be viable, active and abundant in the product to the date of minimum durability. Similar definition could also be applicable for fermented/acidified vegetable milk products. Yogurt is a category of fermented milk characterized by two specific starter cultures used for its fermentation: *Streptococcus thermophilus* and *Lactobacillus delbrueckii* subsp. *bulgaricus*. The requirement of viability of these microorganisms is the same than the one applied to fermented milks.

Although fermented milk products such as yogurts were originally developed simply as a means of preserving the nutrients in milk, it was soon discovered that, by fermenting with different microorganisms, an opportunity existed to develop a wide range of products with different flavors, textures, consistencies and more recently, health attributes. The market now offers a vast array of yogurts to suit all palates and meal occasions. Yogurts come in a variety of textures (e.g. liquid, set and stirred curd), fat contents (e.g. regular fat, low-fat and fat-free) and flavors (e.g. natural, fruit, cereal, chocolate), can be consumed as a snack or part of a meal, as well as a sweet or savory food.

The fermentation process is the most important stage of yogurt manufacture. During this stage, the yogurt gel is formed, and its textural characteristics and distinct flavor are developed (Tamine and Robinson, 2007). The key factor of the fermentation process is the starter culture that acts through biochemical reactions and inductively causes the formation of the curd and the development of flavor components (Walstra et al., 2006a).

Once the milk has been inoculated, it will follow, one of two routes: it will be filled into pots for incubation as set yogurt or it will be fermented in a bulk tank (stirred yogurt). Once the pots for set yogurt have been filled, they will normally be heat-sealed with an aluminium foil lid and placed into holding trays containing up to 24 individual pots (150 mL); for family pots of 500 mL the tray size may be limited to six. The trays are then transferred to an incubation room at 42-43° C. or placed on a conveyor belt that slowly runs through a tunnel operated at the same temperature and followed by blast cooling (Tamime & Robinson, 1999; Anon., 2003). Stirred yogurt is, by contrast, filled into pots as the final retail product, and hence the base material is fermented in bulk. However, no matter what type of yogurt is being produced, the biochemical reactions responsible for the formation of the gel/coagulum are exactly the same. Thus, the only real differences between set and stirred yogurt are the rheological properties of the coagulum, since in the former type the milk is left undisturbed during the incubation period and the resultant gel is in the form of a continuous semi-solid mass, while stirred yogurts are, by contrast, the result of breaking the gel structure at the end of the incubation period and prior to cooling and further processing (Tamime & Robinson, 1999).

An optimum temperature of the thermophilic lactic acid bacteria, i.e., *Streptococcus* subsp. *thermophilus* and *Lactobacillus delbrueckii* subsp. *bulgaricus*, is around 40-45° C. Bacterial fermentation converts lactose into lactic acid, which reduces the pH of milk. During acidification of milk, the pH decreases from 6.7 to ≤4.6. Gelation occurs at pH 5.2 to 5.4 for milk that was given a high heat treatment (Lee and Lucey, 2010).

Physico-chemical mechanisms for the formation of acid milk gels can be divided in three pH regions (Lucey, 2004). When the pH of milk decreases from 6.6 to 6.0, the net negative charge on the casein micelles decreases, which results in a decrease in electrostatic repulsion. Since only a small amount of colloidal calcium phosphate (CCP) is solubilized at pH >6.0, the size of the casein micelles is largely unchanged. As the pH of milk decreases further from pH 6.0 to 5.0, the net negative charge on casein micelles greatly decreases and the charged "hairs" of κ-casein may shrink (or curl up). This results in a decrease in electrostatic repulsion and steric stabilization, which are both responsible for the stability of casein micelles in the original milk. At pH ≤6.0 the rate of solubilization of CCP increases, which weakens the internal structure of casein micelles and increases electrostatic repulsion between the exposed phosphoserine residues. In milk, CCP is completely solubilized in casein micelles by pH ~5.0. During the acidification of milk many of the physicochemical properties of casein micelles undergo considerable change, especially in the pH range 5.5-5.0, including a voluminosity maximum (of the sedimentable caseins), dissociation of the caseins, a slight reduction in the hydrodynamic diameter, solubilization of colloidal calcium phosphate and a maximum in the buffering index (Lucey et al., 1998). High heat treatment of milk causes a shift in gelation pH towards higher pH values. Lucey et al. (1998) suggested that this shift was due to the higher isoelectric pH (~5.3) of β-lactoglobulin, which is the main whey protein. When the pH of milk becomes close to the isoelectric point of casein (pH 4.6), there is a decrease in the net negative charge on casein, which leads to a decrease in electrostatic repulsion between casein molecules. On the other hand, casein-casein attractions increase due to increased hydrophobic and plus-minus (electrostatic) charge interactions (Home, 1998). The acidification process results in the formation of three-dimensional network consisting of clusters and chains of caseins (Mulvihill and Grufferty, 1995).

After the pH of yogurt reaches the value of 4.6, the yogurt is cooled to around 5° C. This inhibits the growth and metabolic reaction of the starter culture and prevents the rise in acidity. Cooling of yogurt can be in one or two phases. One-phase cooling involves the rapid decrease of the coagulum temperature to less than 10° C., where the fermentation process is inhibited leading to yogurt with low viscosity. Two-phase cooling is initiated by rapidly decreasing the temperature to less than 20° C. and then gradually reaching the storage temperature of 5° C. leading to yogurt with an increased viscosity and limited syneresis. This is quite common in the yogurt manufacture process, especially when fruits are to be added (Walstra et al., 2006b).

The determination of incubation time is an essential technical parameter in industrial yogurt production. Due to the complexity of the fermentation process and the great number of factors entangled in yogurt coagulation, prediction of the incubation step is difficult, so it is a common practice to control it empirically (Soukoulis et al, 2007). The end point of the fermentation process is usually defined by the pH value. When the pH end point is specified, by means of the final product quality profile, then online control of the fermentation process can be carried out by monitoring pH. Failure to control and monitor the pH end point leads to discoloration, excessive free whey and excess or insufficient tartness.

However, the industrial pH measurement is usually performed in a discontinuous way. That is because milk protein represents the single biggest challenge for measuring pH in dairy applications. In the fermentation tank, the milk proteins coat the pH sensor and distort or stop the measurement, additionally, use of glass electrodes is not acceptable in the food and beverage industry. The pH probe is sensitive to both drift and protein deposit, so a regular and extent (and therefore labor intensive) cleaning of the pH probe is thus necessary. This, together with the necessity of a recalibration at the start of each new batch of yogurt, makes pH measurement a cumbersome technique for continuous, inline process control of yogurt fermentation in industrial plants (de Brabandere and de Baerdemaeker, 1999).

Conventional lab measurement (manual sampling) is the most common method of monitoring the pH of a process, but manual sampling is time consuming and subject to sample contamination. Even small changes in temperature can result in misleading measurement results. Because of these issues, most pH measurements are taken on an infrequent basis, although this makes tight process control difficult to achieve. In addition, infrequent sampling could potentially result in inconsistent product quality, or a waste of product, additives, and preservatives. Manual sampling is, however, commonly accepted in the industry and operators trust the measurements.

Conventional glass sensors are generally not accepted in food processing applications because of concerns about glass breakage directly in the process stream. In response to this concern, non-glass pH probes based on IsFET (ion selective field effect transistor) technology have been commercially available for inline use. However, these probes are sensitive to extreme pH conditions encountered during normal CIP operations. In particular, exposure to caustic materials at elevated temperatures significantly reduces the useful life of these pH sensors. To overcome this problem, some companies have developed pH sensors based on IsFET technology that can be retracted during CIP operations. That sensors can be automatically cleaned while are retracted (Wesstrom, 2001).

The manual measurements of pH have much greater variation compared to inline continuous measurements, even though the same person was doing the manual measurements with the same sensor. The inline measurement not only provides less variation in the measurement, but the benefits of continuous measurement. Inline continuous measurements provide tighter control and faster response to changes, while also helping reduce labor costs.

The milk fermentation process of yogurt can be described adequately by the evolution of pH and viscosity with respect to time; the model that expresses the evolution of pH during fermentation time is the modified Gompertz models of de Brabandere and de Baerdemaeker (1999) (Equation (1)).

$$pH = pH_0 + (pH_\infty - pH_0)\exp\left\{-\exp\left[\frac{e \cdot \mu}{pH_\infty - pH_0} \cdot (\lambda - t) + 1\right]\right\} \quad (1)$$

$pH_0$, $pH_\infty$=initial and end values of pH respectively; $\mu$ (min$^{-1}$)=maximum rate of pH decrease with time; $\lambda$ (min) =duration of pH lag phase.

Furthermore, the model that describes the evolution of viscosity during fermentation is the modified Gomperz model of Soukoulis, et al. (2007) (Equation (2)).

$$\mu_\alpha = \mu_{\alpha 0} + (\mu_{\alpha 0} - \mu_{\alpha \infty})\exp\left\{-\exp\left[\frac{e \cdot \mu_v}{(\mu_{\alpha 0} - \mu_{\alpha 0})} \cdot (\lambda_v - t) + 1\right]\right\} \quad (2)$$

$\mu_{\alpha 0}$, $\mu_{\alpha \infty}$ (Pa·s)=initial and end values of viscosity respectively; $\mu_v$ (min$^{-1}$)=maximum rate of apparent viscosity; $\lambda_v$ (min)=duration of viscosity lag phase.

In fermented milks industry the definition of the optimal incubation time is significant not only in reducing the manufacturing cost but also in avoiding deterioration of the quality characteristics of the final product. Unfortunately, nowadays there is a lack of a rapid, reliable, and robust monitoring technique, applicable to inline process control, under industrial conditions that overcome the problems related to use of pH-meters, allowing accurately terminate the culture at a well-defined optimal and reproducible quality state.

Changes of the optical properties of milk during coagulation have permitted the development of several devices, more particularly since fibre-optics became widespread. Optical techniques such as light absorbance, transmission and reflectance, over visible and near-infrared (NIR) wavelengths, were employed to assess milk coagulation. Many of those optical methods are very suitable for inline measurement using optical fibers. An optical microscopic method was proposed by Lagaude et al. (2004) for determination of rennet visual flocculation and rheometric gel times and to observe simultaneously structural changes occurring during gel formation. Study of network formation has also been often realized using light scattering. In milk and, especially, in the visible and near infrared ranges, light scattering predominates over absorption. Light scattering is directly related to the rate of aggregation and curd firming if total casein concentration does not vary during the measurements. Indeed, use of optical fibers allows applying different optical configurations for sensor development. Conventional turbidity measurements were one of the first light scattering techniques proposed for monitoring network growth.

A fiber optic sensor technology used to measure light dispersion has been demonstrated to be one of the most promising inline, nondestructive methods for monitoring milk coagulation (Payne et al., 1990, 1993). This technique has become commercially available for inline monitoring of cheese production.

The use of two optical fibres spaced 0.7 mm apart to transport the light is a unique optical configuration that yields a strong signal proportional to the changes that occur in the protein structure during coagulation. Light from a light-emitting diode (LED) is transferred to the milk through a fibre, and the light backscattered (LB) from the milk is transmitted through an adjacent fibre to an optical detector. The LB signal contains information about aggregation of casein micelles and gel assembly during milk coagulation. The LB profile increases sigmoidally as milk coagulation proceeds for acid-, mixed-, or rennet-induced coagulation in cow, goat, and sheep milk (raw and skim) (Payne et al., 1993; Payne and Castillo, 2007; Nicolau et al., 2010). The LB ratio is generated by dividing the voltage from the sensor, V, by the voltage $V_0$ obtained by averaging over the period of 1 min after adding the enzyme. The LB ratio begins with a value of 1 and represents the increase in signal during coagulation.

As was mentioned previously, there is a lack of an efficient, affordable, easy to clean and sanitary, inline pH monitoring sensor, as an alternative to use of pH-meter in dairy industry.

Cimander et al. (2002) follow the course of lab-scale yogurt fermentation using an electronic nose (EN), a near-infrared spectrometer (NIRS) and standard bioreactor probes. The sensor signals were fused using a cascade neural network predicting quantitative process variables (including lactose, galactose and lactate) and qualitative process state variable describing critical process phases, such as the onset of coagulation or the harvest time. The accuracy of the neural network prediction was acceptable and comparable with the off-line reference assay. The results demonstrate that online sensor fusion with the chosen analyzers improves monitoring and quality control of yogurt fermentation with implications to other fermentation processes. In the previous mentioned work, the near infrared spectra did also capture parts of the process variation, some of the wavelengths (e.g. around 800 nm of the NIR spectrum) followed pH and lactose during the first process phase, and a sudden, steep increase in the spectrum at 3 h was observed because of the onset of casein coagulation. Also the NIR signals were correlated with the viscosity of the system. As the texture of the yogurt is decisive for the final quality, NIRS may provide a new way to determine when the fermentation is ready.

In a following similar work (Navrátil et al., 2004), near-infrared (NIR) spectrometry and EN data were used for online monitoring of yogurt and filmjolk (a Swedish yogurt-like sour milk) fermentations. The NIR signals were used to set up empirical partial least-squares (PLS) models for prediction of the cultures' pH and titratable acidity. By using five PLS factors the models yielded acceptable predictions ($R^2$=0.990 and 0.995, SEP=0.35 and 10, respectively) that could be further improved by increasing the number of reliable and precise calibration data. It is demonstrated that analytical NIR and/or EN data in combination with chemometric evaluation have potential to become a useful tool in monitoring of industrial yogurt manufacture. However, successful long-term operation requires a sufficient amount of reliable calibration data.

Visible/near infrared spectroscopy (Vis/NIRs) technique was applied by Shao and He (2009) to evaluate sugar and pH value in different commercial brands of yogurt. Partial least squares (PLS) analysis and least squares support vector machine (LS-SVM) were implemented for calibration models. In the LS-SVM model, the correlation coefficient and the root mean square error of prediction for pH were 0.9208, 0.0327 respectively. The overall results indicated that Vis/NIRs combined with LS-SVM models had the capability to predict the soluble solids content and pH value of yogurt, though the results showed that it is difficult to select one or a few wavelengths for their accurate prediction.

REFERENCES

Anon. (2003). Dairy Processing Handbook, 2nd revised edn, Tetra Pak Processing Systems AB, Lund, Sweden.

Castillo, M.; Payne, F. A.; Hicks, C. L.; Laencina, J.; Lopez, M. B. (2002). Effect of calcium and enzyme in cutting time prediction of coagulating goats' milk using a light scattering sensor. International Dairy Journal, 12: 1019-1023.

Castillo, M.; Payne, F. A.; Hicks, C. L.; Lopez, M. B. (2000). Predicting cutting and clotting time of coagulating goats' milk using diffuse reflectance: Effect of pH, temperature and enzyme concentration. International Dairy Journal, 10: 551-562.

Cimander, C.; Carlsson, M.; Mandenius, C. (2002). Sensor fusion for online monitoring of yoghurt fermentation. Journal of Biotechnology 99: 237-248.

De Brabandere, A. G.; de Baerdemaeker, J. G. (1999). Effects of process conditions on the pH development during yogurt fermentation. J. Food Eng. 41: 221-227.

Horne, D. S. (1998). Casein interactions: Casting light on the Black Boxes, the structure in dairy products. Int. Dairy J. 8:171-177.

Lee, W. J.; Lucey, J. A. (2010). Formation and physycal properties of yogurt. Asian-Aust. J. Anim. Sci., 23(9): 1127-1136.

Lucey, J. A. (2004). Formation, structural properties and rheology of acid-coagulated milk gels. In Cheese: Chemistry, Physics and Microbiology. Vol. 1. General Aspects (Ed. P. F. Fox, P. L. H. McSweeney, T. M. Cogan and T. P. Guinee). 3rd ed. Elsevier Academic Press, London. pp. 105-122.

Lucey, J.; Tamehana, M.; Singh, H.; Munro, P. (1998). Effect of interactions between denatured whey proteins and casein micelles on the formation and rheological properties of acid skim milk gels. J. Dairy Res. 65:555-567.

Mulvihill, D. M. and M. B. Grufferty. (1995). Effect of thermal processing on the coagulability of milk by acid. In Heatinduced Changes in Milk. Special Issue No. 9501 (Ed. P. F. Fox). International Dairy Federation, Brussels. pp. 188-205.

Navrátil, M.; Cimander, C.; Mandenius, C. (2004). Online Multisensor Monitoring of Yogurt and Filmjölk Fermentations on Production Scale. J. Agric. Food Chem. 52: 415-420.

Nicolau, N.; Castillo, M.; Buffa, M; O'Callaghan, D. J.; Guamis, B. (2010). Estudio de la coagulación de leche de oveja mediante monitorización con un sensor óptico. Actas del VI Congreso Español de Ingeniería de Alimentos, Logroño, España. ISBN: 978-84-7359-654-1.

O'Callaghan, D. J.; O'Donnell, C. P.; Payne, F. A. (2000). Online sensing techniques for coagulum setting in renneted milks. Journal of Food Engineering, 43: 155-165.

O'Callaghan, D. J.; O'Donnell, C. P.; Payne, F. A. (1999). A comparison of online techniques for determination of curd setting time using cheese milks under different rates of coagulation. Journal of Food Engineering, 41: 43-54.

Payne, F. A.; Castillo M. 2007. Light backscatter sensor applications in milk coagulation. In: Encyclopedia of Agricultural, Food, and Biological Engineering. Volume 1, Edition 1, Pp. 1-5. Heldman, D., Ed. Taylor & Francis Group, Boca Raton. ISBN: 978-0-8247-0938-9 (hardback); 978-0-8247-0937-2 (electronic).

Payne, F. A.; Hicks, C. L.; Shen, P. S. (1993). Predicting optimal cutting time of coagulating milk using diffuse reflectance. J. Dairy Sci. 7648-7661.

Payne, F. A.; Madangopal, S.; Hicks, C. L.; Shearer, S. A. (1990). Fiber optic milk coagulation sensor for cut-time detection. Food Processing Automation Conference, American Society of Agricultural Engineers, St. Joseph. Mich., Publication 02-90, 173.

Shao, Y.; He, Y. (2009). Measurement of Soluble Solids Content and pH of Yogurt Using Visible/Near Infrared Spectroscopy and Chemometrics. Food Bioprocess Technol 2: 229-233.

Soukoulis, C.; Panagiotidis, P.; Koureli, R.; Tzia, C. (2007). Industrial yogurt manufacture: Monitoring of fermentation process and improvement of final product quality. J. Dairy Sci. 90, 2641-2654.

Tabayehnejad, N.; Castillo, M.; Payne, F. A. (2011). Comparison of total milk-clotting activity measurement precision using the Berridge clotting time method and a proposed optical method. Journal of Food Engineering, 108: 549-556.

Walstra, P.; Wouters, J. T. M.; Geurts, T. J. (2006a). Chapter 22 Fermented milks. In Dairy Science and Technology; Taylor & Francis Group, LLC: Boca Raton, Fla., USA, pp. 551-573.

Walstra, P.; Wouters, J. T. M.; Geurts, T. J. (2006b). Chapter 11 Cooling and freezing. In Dairy Science and Technology; Taylor & Francis Group, LLC: Boca Raton, Fla., USA, pp. 297-307.

Wesstrom, O. (2001). Endress+Hauser, Inc. white paper: Inline pH Measurement for the Food/Dairy and Beverage Industry.

DESCRIPTION OF THE INVENTION

Embodiments of the present invention provide according to a first aspect a method for determining pH values of fermented/acidified animal/vegetable milk products from inline optical measurements. The method comprises, as commonly in the field: emitting light into a fermented/acidified animal/vegetable milk product; optically detecting scattering light coming from said fermented/acidified animal/vegetable milk product, generated from said emitted light once received therein, to collect scattered light data; calculating by a computing device including one or more processors running an algorithm at least one value of a variable from the collected scattered light data; and obtaining, by said computing device a pH value of the fermented/acidified animal/vegetable milk product by using said at least one calculated value of a variable.

In a characteristic manner, and on contrary to the known proposals, in the proposed method a single wavelength is used for collecting the scattered light data.

In accordance with an embodiment, the single wavelength used is comprised in the range of 700-1100 nm. In a preferred embodiment, the single wavelength is 880 nm.

In accordance with the proposed method, the calculation of said at least one value of a variable is performed when a gel formation process of the fermented/acidified milk product starts. Preferably, said variable is a light backscatter ratio at a given time.

In accordance with an embodiment, following equation $$pH = \frac{a + bR}{1 + cR + dR^2},$$

directly correlating the pH value and the light backscatter ratio, is used by said computing device, in which a, b, c and d are correlation coefficients. Moreover, the correlation coefficients may be adjusted by the computing device in said equation taking into account changes in parameters influencing the light backscatter ratio including at least a protein content, fat content and coagulation temperature of the fermented/acidified animal/vegetable milk product.

In accordance with an embodiment, the collecting of light data is performed a plurality of times, being the values of said variable calculated for each of said plurality of times.

In accordance with the proposed method, the fermented/acidified animal/vegetable milk product may be any of: yogurt, kumis or other fermented milks, acid-induced coagulation cheese, mixed-induced coagulation cheese and/or fermented/acidified almond, rice, soy and tiger nut vegetable milks, among others.

In addition, the fermented/acidified milk product may be any of a whole, skimmed or semi-skimmed fermented/acidified animal/vegetable milk product with or without any other authorized additional ingredient (i.e. fruit pieces, fiber, cereals, etc.).

Embodiments of the present invention provide according to a second aspect a system for determining pH values of fermented/acidified animal/vegetable milk products from inline optical measurements. The system comprising light means for emitting light into a fermented/acidified animal/vegetable milk; optical detection means for optically detecting scattering light coming from said fermented/acidified animal/vegetable milk product, to collect scattered light data; and processing means included in a computing device for processing the collected scattered light data for calculating at least one value of a variable to be used to obtain a pH value of the fermented/acidified animal/vegetable milk product.

In the proposed system, on contrary of the known proposals in the field, said optical detection means are arranged and configured to collect the scattered light data at a single wavelength.

Preferably, in accordance with an embodiment, said optical detection means includes an optical sensor operating under said single wavelength. In this case, the optical detection means may include optical adjustable means enabling to operate under said single wavelength.

In accordance with yet another embodiment, the processing means are configured for calculating said value of a variable by processing the collected scattered light data according to an algorithm configured to be run when a gel formation process of the fermented/acidified animal/vegetable milk product starts, said algorithm implementing the method steps of the first aspect of the invention.

The light means may comprise a first optical fibre and a light source, such as a LED or a xenon flash lamp among others, arranged for emitting light into said gel through said first optical fibre, said optical detection means comprises a second optical fibre placed adjacent to said first optical fibre and an optical detector arranged for receiving the light transmitted through said second optical fibre coming from the gel, converting them into electrical signals, corresponding to said collected light data, and delivering said electrical signals to the processing means.

BRIEF DESCRIPTION OF THE DRAWINGS

The previous and other advantages and features will be more fully understood from the following detailed description of embodiments, with reference to the attached figures, which must be considered in an illustrative and non-limiting manner, in which.

DETAILED DESCRIPTION OF PREFERRED EMBODIMENTS

Present invention provides a method and a system for determining pH values of fermented/acidified animal/vegetable milk products from inline optical measurements.

The proposed invention requires simpler equipment, which is easy to calibrate and clean, not expensive, and which can work, for the practical applications, based only on empirical parameters, obtained by calibration in real conditions.

Figure 1:
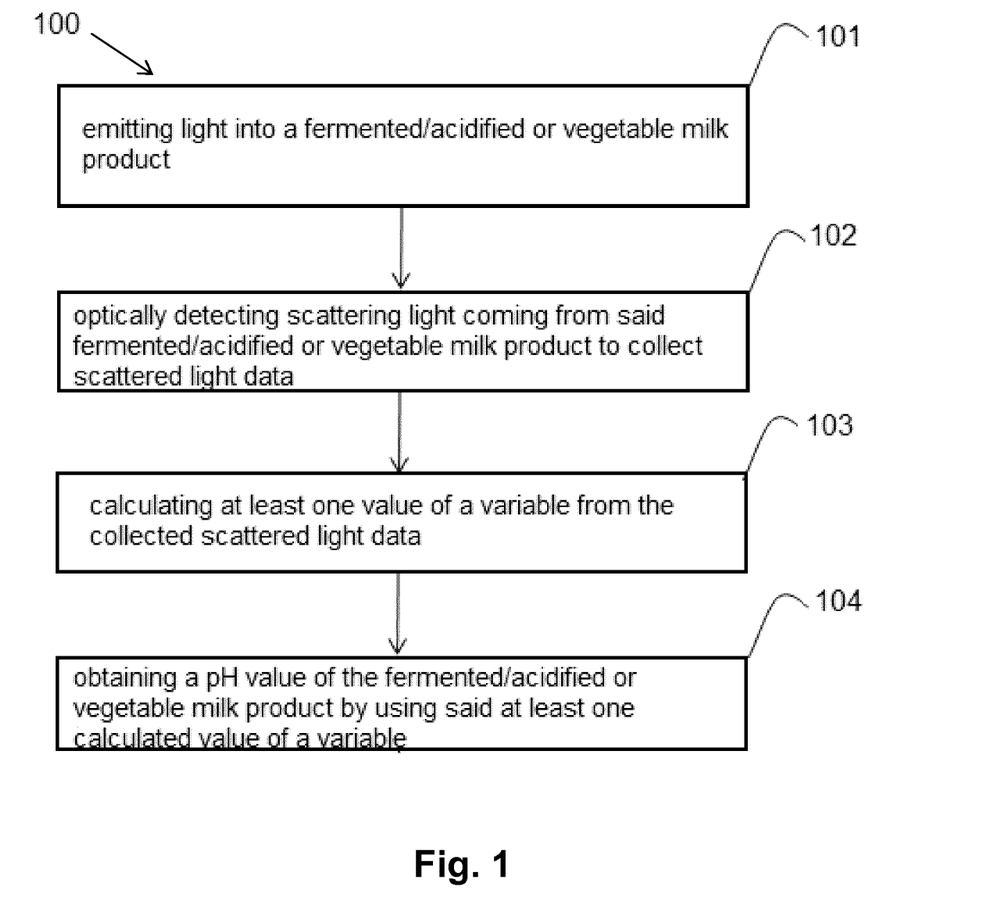
FIG. 1 is a flow diagram illustrating an example of a method for determining pH values of fermented/acidified animal/vegetable milk products from inline optical measurements according to one embodiment of the present invention.

FIG. 1 shows therein an embodiment of a method 100 for determining pH values of fermented/acidified animal/vegetable milk products from inline optical measurements. The method 100 includes, step 101, emitting light into a fermented/acidified animal/vegetable milk product. Then, at step 102, scattering light from the fermented/acidified animal/vegetable milk product is optically detected to collect, at a single wavelength, scattered light data. At that time, step 103, at least one value of a variable is calculated (by a computing device with at least one processor running an algorithm) from the collected scattered light data. Finally, at step 104, a pH value of the fermented/acidified animal/vegetable milk product is obtained by using said calculated value.

Figure 4:
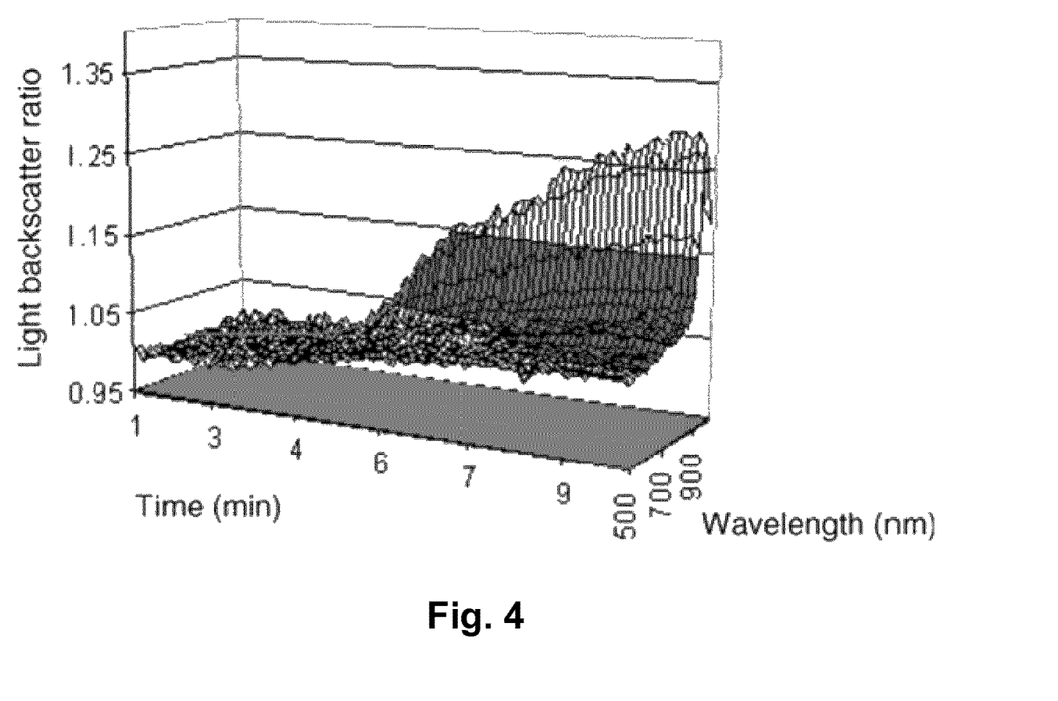
FIG. 4 is an illustration representing light backscatter ratio evolution as a function of time for different wavelengths.

According to a preferred embodiment, the single wavelength is chosen at 880 nm, not limitative, as in the proposed method the single wavelength may have any value comprised in the range of 700-1100 nm. Even, the single wavelength can be chosen to have any value comprised in a broader range, for instance 500-1200 nm. As it can be observed in FIG. 4, a range of wavelengths exists around 900 nm were light backscatter ratio increases sigmoidally during coagulation; therefore, in the proposed method the single wavelength can be chosen to have any value comprised in said ranges.

In addition, present invention may directly correlate the evolution of the light backscatter ratio (R) with the pH and use a mathematical function to adjust the curve of that relationship. In particular, the proposed method adjusts only the curve from pH 5.2, because around that pH, gelation starts and light backscatter ratio increases significantly, as particle size increases during network formation due to casein micelle cross-linking.

In a preferred embodiment, said mathematical function is $$\mathrm{pH} = \frac{a + bR}{1 + cR + dR^2}, \quad (3)$$

where a, b, c and d are correlation coefficients.

Next an example of a particular embodiment of present invention will be detailed. In this case, the fermented/acidified animal/vegetable milk product is a low-fat yogurt (not limitative as present invention is also useful for kumis or other fermented milks, acid-induced coagulation cheese, mixed-induced coagulation cheese and/or fermented/acidified almond, rice, soy and tiger nut vegetable milks, among many other milk products).

A complete randomized factorial design with three replicates is used to evaluate the proposed equation for optical prediction of pH values using equation (3) during fermentation of low-fat yogurt with inulin as fat replacer. Yogurt fermentation tests were conducted with three fat concentrations (0.4, 1.6 and 3.6%) and three inulin levels (0, 1.6 and 3.2%). The coagulation process was monitored using an inline light backscatter sensor operated at 880 nm. The whole experiment was run in triplicate. The changes occurred in the protein structure during milk coagulation were correlated to the signal changes derived from the optical sensor and the light backscatter ratio increased as aggregation and gel assembly proceeded.

Whole, semi-skimmed and skimmed UHT commercial milk was used. Low heat powder milk was added to increase the solids content and standardize the protein level to 4.0% in all samples. Fat levels were adjusted by addition of homogenized cream. Samples were prepared the day of the test and underwent heat treatment at 90° C. for 5 min. A stock culture was prepared using lyophilized commercial yogurt starter, which was reactivated by adding 130 mg/L in reconstituted milk with 12% solids. This stock culture was incubated to pH 5.0 in a thermostatic bath at 43° C. and then aseptically filled into vials of 2 g each, and was frozen at −80° C. From the stock culture a working culture was prepared for each test by inoculating 2% on reconstituted milk and incubating to pH 5.0. In each test the sample made according to the experimental design was warmed to 43° C., inoculated with 2% of working culture and immediately, two aliquots of ~80 mL were placed in the optical sensor vessels with pH probes (FIG. 2) and the near infrared light backscatter monitoring software was started.

Figure 2:
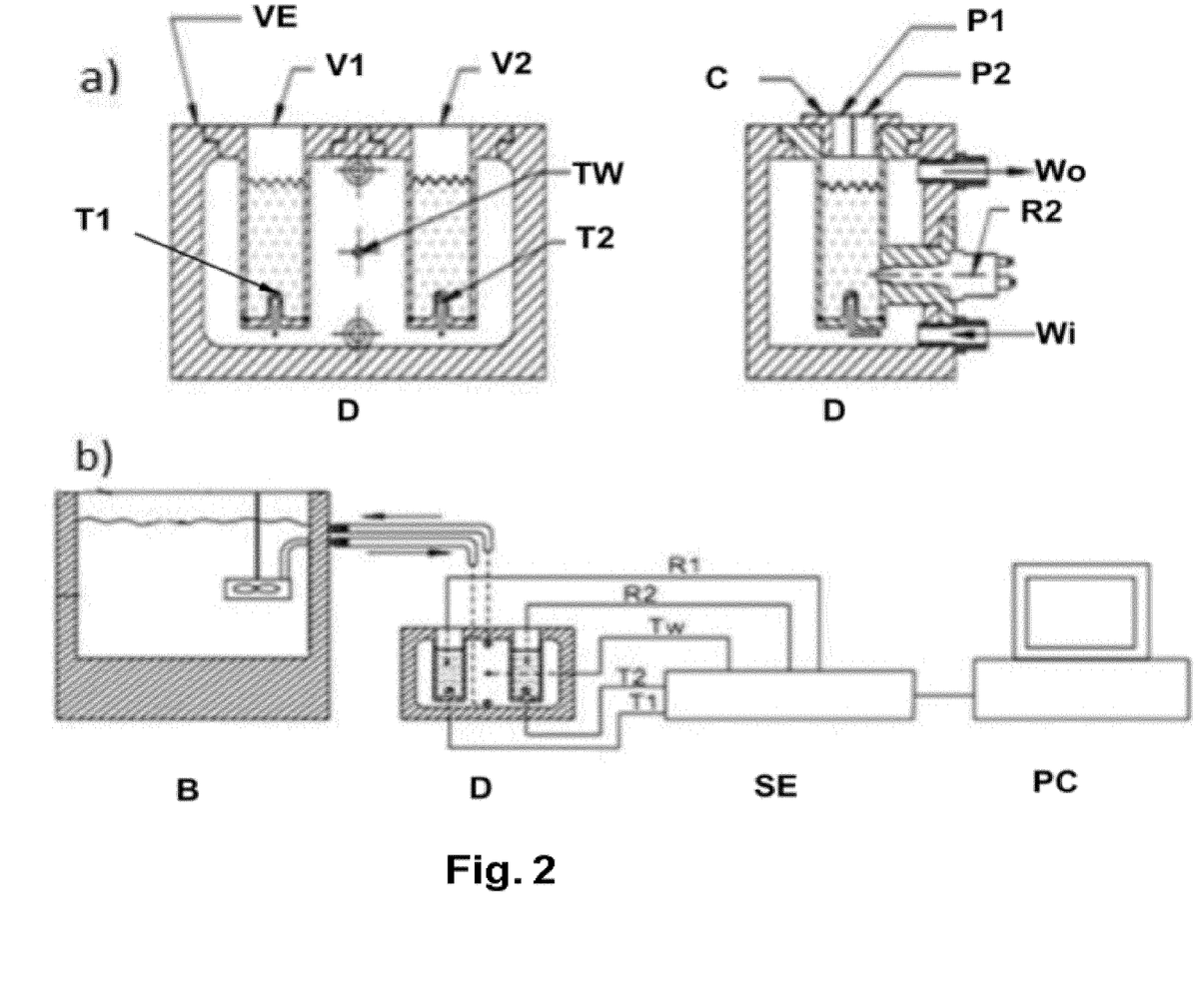
FIG. 2 Schematic of the coagulation measurement apparatus used to measure near infrared light backscatter (R) during milk coagulation (Tabayehnejad et al., 2011).

The equipment used to determine the near infrared light backscatter profile at 880 nm during yogurt culture was designed at the University of Kentucky (FIG. 2). A detailed description of it was presented in the work of Tabayehnejad et al. (2011). The device D, as shown in FIG. 2a (side view, left, and end view, right) has two vats V1, V2 of 98 mL (FIG. 2a) capacity to monitor coagulation in two samples simultaneously and make accurate comparisons. The device D has a water tank surrounding the vats V1, V2 with a water thermistor Tw placed therein, a water input Wi and a water output Wo for the water tank, vats thermistors T1, T2, optical fibres pairs R1, R2, and an upper cap C, for each vat V1, V2, with a pH port P1 and a stir port P2.

FIG. 2b shows the setup of the entire laboratory measurement, where an electronic system SE, which is controlled by a computer PC, has several inputs connected to, respectively, water thermistor Tw, vats thermistors T1, T2, optical fibres pairs R1, R2 for emitting light and receiving the scattered light to be detected by corresponding light detectors (not shown). The circulating water between the water bath B and the outside of the coagulation vats V1, V2, via Wi and Wo, regulated the temperature of milk samples in the vats V1, V2.

This sensor transmitted near infrared light at 880 nm through two 600 μm diameter fibers. One fiber transmitted infrared radiation into the milk sample while the other fiber transmitted the radiation scattered by the milk particles to a silicon photo-detector. For calibration, the optic sensor was zeroed by excluding light and adjusting the output voltage to 1 V. Response data were collected every 2 s. The initial voltage response ($V_0$) was calculated by averaging the first ten data points after correction for 1 V offset. The optical data generated in the vats were collected at intervals of 6 s. The light backscatter profile was calculated by dividing the voltage output from the detector by the average of the first ten voltage data points collected after the enzyme addition, according to the procedure described by Castillo et al. (2000).

Figure 3:
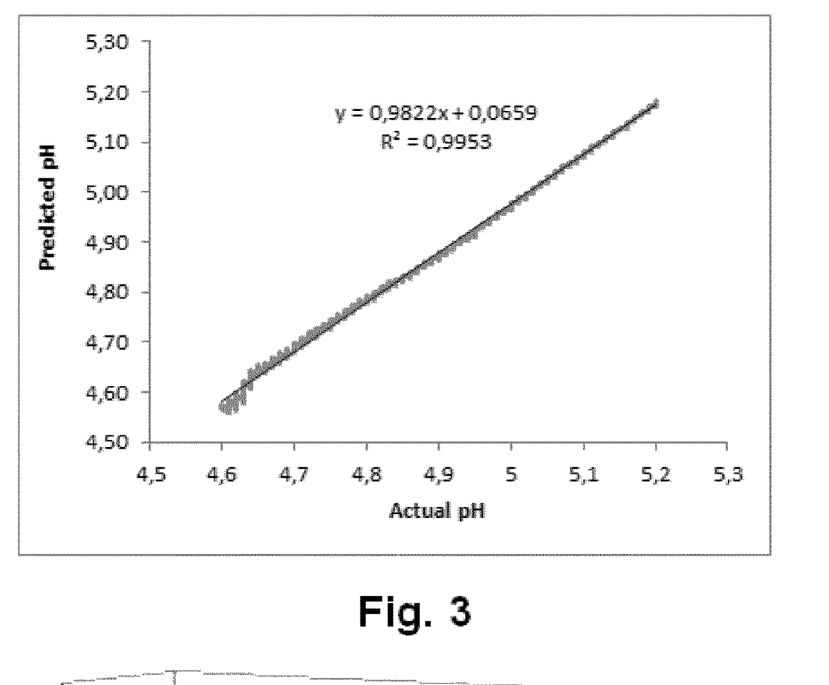
FIG. 3 Measured vs Predicted pH during yogurt fermentation at 43° C. with 2% of inoculum.

Using the light backscatter ratio obtained with the optic sensor it was possible to predict the pH using the proposed equation (3). FIG. 3 shows that the fitting was very good in the different coagulation conditions evaluated, where y=predicted pH values, x=actual pH values, and $R^2$ is the determination coefficient for the linear regression between observed and predicted pH values.

A person skilled in the art could introduce changes and modifications in the embodiments described without departing from the scope of the invention as it is defined in the attached claims.

The invention claimed is:

1. A method for determining pH values of fermented/acidified milk/vegetable milk products, the method comprising:
   a. emitting light into a fermented/acidified animal/vegetable milk product, inline and during processing of the fermented/acidified milk/vegetable milk product;
   b. optically detecting scattered light coming from said fermented/acidified animal/vegetable milk product, generated from said emitted light once received therein, to collect scattered light data;
   c. calculating at least one value of a variable from the collected scattered light data by use of a computing device running an algorithm, said computing device including one or more processors; and
   d. obtaining a pH value of the fermented/acidified animal/vegetable milk product by using the calculated at least one value of a variable from the collected scattered light data, the obtaining of said pH value being performed by said computing device,
   wherein the method is characterized in that a single wavelength is used for collecting the scattered light data, and
   wherein the pH value is less than or equal to 5.2.

2. The method of claim 1, wherein the processing of the fermented/acidified milk/vegetable milk product comprises forming a gel, and wherein said calculating of at least one value of a variable by said computing device is performed when starts the gel begins to form.

3. The method of claim 1, wherein said variable is a light backscatter ratio at a given time.

4. The method of claim 3, wherein said computing device in step d) utilizes the following equation:

$$pH = \frac{a + bR}{1 + cR + dR^2},$$

wherein a, b, c and d are correlation coefficients, and R is a light backscatter ratio, to directly correlate said pH value and said backscatter ratio,
   wherein said light backscatter ratio contains information about aggregation during coagulation of the fermented/acidified milk/vegetable milk product.

5. The method of claim 4, wherein said correlation coefficients are adjusted by the computing device in said equation by taking into account changes in parameters influencing the light backscatter ratio including at least a protein content, a fat content and a coagulation temperature of the fermented/acidified animal/vegetable milk product.

6. The method of claim 1, further comprising performing said collecting of light data a plurality of times, and calculating the values of said variable for each of said plurality of times.

7. The method of claim 1, wherein the fermented/acidified animal/vegetable milk product are at least one of: yogurt, kumis or other fermented milks, acid-induced coagulation cheese, mixed-induced coagulation cheese and/or fermented/acidified almond, rice, soy and tiger nut vegetable milks.

8. The method of claim 7, wherein the fermented/acidified animal/vegetable milk product comprises at least one of a whole, skimmed or semi-skimmed fermented/acidified milk product, with or without any other additional ingredient.

9. The method of claim 1, wherein said single wavelength used is comprised in the range of 700-1100 nm.

10. The method of claim 9, wherein the single wavelength is 880 nm.

11. A system for determining pH values of fermented/acidified animal/vegetable milk products, the system comprising:
    light means for emitting light into a fermented/acidified animal/vegetable milk product, inline and during processing of the fermented/acidified milk/vegetable milk product;
    optical detection means for optically detecting scattered light coming from said fermented/acidified animal/vegetable milk product, to collect scattered light data; and
    a computing device including processing means, said processing means programed to perform the method according to claim 1,
    wherein the system is characterized in that said optical detection means is configured to collect the scattered light data at a single wavelength.

12. The system of claim 11, wherein said optical detection means includes an optical sensor operating under said single wavelength.

13. The system of claim 11, wherein said optical detection means are adjustable so as to operate under said single wavelength.

14. The system of claim 11, wherein the processing of the fermented/acidified milk/vegetable milk product comprises forming a gel, and wherein said processing means are configured for calculating said value of a variable by processing the collected scattered light data according to an algorithm configured to be run when the gel begins to form.

15. The system of claim 11, wherein said light means comprise a first optical fiber and a light source arranged for emitting light into said fermented/acidified animal/vegetable milk through said first optical fiber, said optical detection means comprises a second optical fiber placed adjacent to said first optical fiber and an optical detector arranged for receiving the light transmitted through said second optical fiber coming from the fermented/acidified animal/vegetable milk, converting them into electrical signals, corresponding to said collected light data, and delivering said electrical signals to the processing means.

16. A method for determining pH values of fermented/acidified milk/vegetable milk products, the method comprising:
   a. emitting light into a fermented/acidified animal/vegetable milk product, inline and during processing of the fermented/acidified milk/vegetable milk product;
   b. optically detecting scattered light coming from said fermented/acidified animal/vegetable milk product, generated from said emitted light once received therein, to collect scattered light data;
   c. calculating at least one value of a variable from the collected scattered light data by use of a computing device running an algorithm, said computing device including one or more processors; and
   d. obtaining a pH value of the fermented/acidified animal/vegetable milk product by using the calculated at least one value of a variable from the collected scattered light data, the obtaining of said pH value being performed by said computing device,
   wherein the method is characterized in that a single wavelength is used for collecting the scattered light data, and
   wherein the processing of the fermented/acidified milk/vegetable milk product comprises forming a gel, and wherein said calculating of at least one value of a variable by said computing device is performed when the gel begins to form.

17. A system for determining pH values of fermented/acidified animal/vegetable milk products, the system comprising:
   light means for emitting light into a fermented/acidified animal/vegetable milk product, inline and during processing of the fermented/acidified milk/vegetable milk product;
   optical detection means for optically detecting scattered light coming from said fermented/acidified animal/vegetable milk product, to collect scattered light data; and
   a computing device including processing means, said processing means programed to perform the method according to claim 16,
   wherein the system is characterized in that said optical detection means is configured to collect the scattered light data at a single wavelength.

18. A method for determining pH values of fermented/acidified milk/vegetable milk products, the method comprising:
   a. emitting light into a fermented/acidified animal/vegetable milk product, inline and during processing of the fermented/acidified milk/vegetable milk product;
   b. optically detecting scattered light coming from said fermented/acidified animal/vegetable milk product, generated from said emitted light once received therein, to collect scattered light data;
   c. calculating at least one value of a variable from the collected scattered light data by use of a computing device running an algorithm, said computing device including one or more processors; and
   d. obtaining a pH value of the fermented/acidified animal/vegetable milk product by using the calculated at least one value of a variable from the collected scattered light data, the obtaining of said pH value being performed by said computing device,
   wherein the method is characterized in that a single wavelength is used for collecting the scattered light data,
   wherein said computing device utilizes the followina eauation:

$$pH = \frac{a + bR}{1 + cR + dR^2},$$

where a, b, c and d are correlation coefficients, and R is a light backscatter ratio, to directly correlate said pH value and said backscatter ratio, and
   wherein said light backscatter ratio contains information about aggregation during coagulation of the fermented/acidified milk/vegetable milk product.

19. A system for determining pH values of fermented/acidified animal/vegetable milk products, the system comprising:
   light means for emitting light into a fermented/acidified animal/vegetable milk product, inline and during processing of the fermented/acidified milk/vegetable milk product;
   optical detection means for optically detecting scattered light coming from said fermented/acidified animal/vegetable milk product, to collect scattered light data; and
   a computing device including processing means, said processing means programed to perform the method according to claim 18,
   wherein the system is characterized in that said optical detection means is configured to collect the scattered light data at a single wavelength.

* * * * *